(12) United States Patent
Tripier et al.

(10) Patent No.: US 9,884,881 B2
(45) Date of Patent: Feb. 6, 2018

(54) CHELATES OF LEAD (II) AND BISMUTH (III) BASED ON TRANS-DI-N-PICOLINATE TETRAAZACYCLOALKANES

(71) Applicants: CNRS—CENTRE NATIONAL DE LA RECHERCHE SCIENTIFIQUE, Paris (FR); UNIVERSITE DE BRETAGNE OCCIDENTALE, Brest (RE)

(72) Inventors: Raphael Tripier, Kersaint Plabennec (FR); Carlos Platas-Iglesias, Bergondo-Coruna (ES); Luis Lima, Lisboa (PT); Maryline Beyler, Brest (FR)

(73) Assignees: CNRS—Centre National de la Recherche Scientifique, Paris (FR); Universite de Bretagne Occidentale, Brest (FR)

( * ) Notice: Subject to any disclaimer, the term of this patent is extended or adjusted under 35 U.S.C. 154(b) by 0 days.

(21) Appl. No.: 14/895,990

(22) PCT Filed: Jun. 5, 2014

(86) PCT No.: PCT/EP2014/061723
§ 371 (c)(1),
(2) Date: Dec. 4, 2015

(87) PCT Pub. No.: WO2014/195416
PCT Pub. Date: Dec. 11, 2014

(65) Prior Publication Data
US 2016/0115187 A1 Apr. 28, 2016

(30) Foreign Application Priority Data
Jun. 6, 2013 (FR) ...................................... 13 55212

(51) Int. Cl.
| C07F 7/24 | (2006.01) |
| C07F 9/94 | (2006.01) |
| C07D 401/06 | (2006.01) |
| A61K 51/04 | (2006.01) |
| C07K 16/00 | (2006.01) |
| A61K 47/68 | (2017.01) |

(52) U.S. Cl.
CPC ............... *C07F 9/94* (2013.01); *A61K 47/68* (2017.08); *A61K 51/0482* (2013.01); *C07D 401/06* (2013.01); *C07F 7/24* (2013.01); *C07K 16/00* (2013.01)

(58) Field of Classification Search
None
See application file for complete search history.

(56) References Cited

PUBLICATIONS

Translation of the International Search Report for PCT/EP2014/061723 dated Jul. 14, 2014.

Aurora Rodriguez-Rodriguez et al: "Lanthanide(III) Complexes with Ligands Derived from a Cyclen Framework Containing Pyridinecarboxylate Pendants. The Effect of Steric Hindrance on the Hydration Number", Inorganic Chemistry, vol. 51, No. 4, Feb. 20, 2012 (Feb. 20, 2012), pp. 2509-2521, XP055083216, ISSN: 0020-1669, DOI: 10.1021/ic202436j.

Hyun A Song et al: "Efficient Bifunctional Decadentate Ligand 3p-C-DEPA for Targeted [alpha]-Radiommunotherapy Applications", Bioconjugate Chemistry, vol. 22, No. 6, Jun. 15, 2011 (Jun. 15, 2011), pp. 1128-1135, XP055083258, ISSN: 1043-1802, DOI: 10.1021/bc100586y.

Diane E. Milenic et al: "In Vivo Evaluation of Bismuth-Labeled Monoclonal Antibody Comparing DTPA-Derived Bifunctional Chelates", Cancer Biotherapy & Radiopharmaceuticals, Jan. 1, 2001 (Jan. 1, 2001), pp. 133-146, XP055083260, Retrieved from the Internet: URL:http://online.liebertpub.comjdoijpdfplus/10.1089/108497801300189227 [retrieved on Oct. 9, 2013].

Luis M.P. Lima et al: "Monopicolinate Cyclen and Cyclam Derivatives for Stable Copper(II) Complexation", Inorganic Chemistry, vol. 51, No. 12, Jun. 18, 2012 (Jun. 18, 2012), pp. 6916-6927, XP055083402, ISSN: 0020-1669, DOI: 10.1021/ic300784v.

Halime Z et al: "Coordination of bismuth and lead in porphyrins: Towards an in-situ generator for alpha-radiotherapy?", Biochimie. Masson, Paris, FR, vol. 91, No. 10, Oct. 1, 2009 (Oct. 1, 2009), pp. 1318-1320, XP026583914, ISSN: 0300-9084, DOI: 10.1016/J.BIOCHI.2009.03.001, [retrieved on Mar. 12, 2009].

Morfin J Fetal: "Bismuth(III) complexes with tetra-pyridylmethyl-cyclen", Inorganica Chimica Acta, Elsevier BV, NL, vol. 362, No. 6, Apr. 20, 2009 (Apr. 20, 2009), pp. 1781-1786, XP026053555, ISSN: 0020-1693, DOI: 10.1016/J.ICA.2008.08.013, [retrieved on Aug. 28, 2008].

Morfin J Fetal: "Bismuth (III) coordination to cyclen and cyclam bearing four appended groups", Polyhedron, Pergamon Press, Oxford, GB, vol. 28, No. 17, Nov. 16, 2009 (Nov. 16, 2009), pp. 3691-3698, KP026722154, ISSN: 0277-5387, DOI: 10.1016/J.POLY.2009.08.003, [retrieved on Aug. 11, 2009].

*Primary Examiner* — Noble E Jarrell
(74) *Attorney, Agent, or Firm* — Thomas | Horstemeyer, LLP (57) ABSTRACT

The invention relates to a chelate resulting from the complexing of a trans-di-N-picolinate tetraazacycloalkane ligand with a metal cation, said ligand corresponding to formula (A) wherein n is equal to 0 or to 1, R is H or a C1-C18 alkyl radical, and R' is H or a C1-C18 alkyl radical, said metal cation being a cation of a metal selected from the group consisting of lead (II) and bismuth (III). The invention is applicable in the field of lead trapping and alpha-radioimmunotherapy.

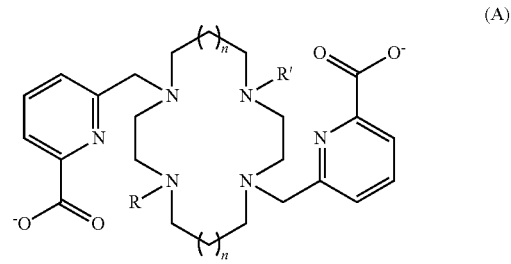

(A)

12 Claims, 4 Drawing Sheets

CHELATES OF LEAD (II) AND BISMUTH (III) BASED ON TRANS-DI-N-PICOLINATE TETRAAZACYCLOALKANES

CROSS REFERENCE TO RELATED APPLICATION

This application is the 35 U.S.C. §371 national stage application of PCT Application No. PCT/EP2014/061723, filed Jun. 5, 2014, which claims priority to and the benefit of, FR Patent Application No. 1355212, filed Jun. 6, 2013, both of which are herein incorporated by reference in their entirety.

FIELD OF THE INVENTION

The invention pertains to the field of chemistry.

More specifically, the invention pertains to chelates resulting from the complexation of tetraazacycloalkane type ligands with metal cations.

In particular, the invention pertains to such chelates based on tetraazacycloalkane type ligands having high affinity with bismuth (III) as well as lead (II), said ligands being thus capable of getting complexated with either one of these elements.

The invention can find application especially in the field of alpha radio-immunotherapy.

PRIOR ART

Lead is an abundantly used element which however is a pollutant that can be assimilated by living organisms and stored in their tissues, causing damage to these tissues. Most cases of lead poisoning result from inhalation or ingestion of lead (II). Infants are especially affected because they can assimilate up to 50% of the ingested lead, giving rise to severe neurological and hematological disorders. After ingestion into the gastrointestinal tract, the lead collects in soft tissues and especially in the brain, the kidneys and the liver where it binds with the thiol and phosphate groups in proteins, nucleic acids and cell membranes. The search for chelates capable of trapping lead (II) is a major challenge and the efficient complexation of this metal ion remains one of the major aspects of coordination chemistry.

Alpha radio-immunotherapy for its part is a technique of therapeutic treatment considered for the treatment of cancers but has not yet shown any effective clinical application for the time being.

This technique implements a radio-pharmaceutical agent including a radioactive isotope emitting alpha radiation, associated with a biological vector such as a monoclonal antibody. Such a radio-pharmaceutical agent thus vectored is aimed at targeting certain major cells as precisely as possible, especially cancer cells, owing to their antigenic properties, in order to destroy them.

Unlike beta radiation, alpha radiation has a short pathway into human tissues. Its energy is therefore absorbed in a smaller area, resulting in a more efficient destruction of cancer cells with minimum damage to healthy tissues (T. M. Behr, M. Behe, M. G. Stabin, E. Wehrmann, C. Apostolidis, R. Molinet, F. Strutz, A. Fayyazi, E. Wieland, S. Gratz, L. Koch, D. M. Goldenberg, W. Becker, Cancer Res., 1999, 59, 2635-2643).

As such, alpha emitters are therefore being preferred as being ideal for the specific treatment of small tumors, cases of spreading of a disease or micro-metastatic diseases.

Among alpha emitters currently being used for alpha radio-immunotherapy type applications, it is especially the $^{212}Bi$ and $^{213}Bi$ emitters that are being studied.

However, the use of such emitters is coming up against several obstacles.

First of all, the $^{212}Bi$ and $^{213}Bi$ emitters like many radioactive metals cannot be used in their free ion form because of their high toxicity.

Besides, the half-lives of $^{212}Bi$ and $^{213}Bi$ ($t_{1/2}$=60.6 minutes and $t_{1/2}$=45.6 minutes respectively) are not long enough to ensure that they can be efficiently prepared and transported towards their targets.

Finally, bismuth hydroxides precipitate very quickly once the salts of this metal are placed in water solution at pH values of over 2.

With regard to the first of these problems, it will be noted that there are known ways of confining radioactive metal cations by means of tetraaazacycloalkane macrocyclic ligands to form chelates that conceal the toxicity of these cations. The macrocyclic pattern can be functionalized through these four nitrogen atoms, using four additional chelating groups in order to coordinate a metal cation in a very stable manner.

Thus, the derivatives of 1,4,8,11-tetraazacyclotetradecane and 1,4,7,10-tetrazacyclododecane, such as especially DOTAM and DOTA are ligands known for efficiently complexating numerous radioactive metal cations.

They have also found application in the medical field as contrast agents for (DOTA-$Gd^{3+}$) MRI (A. E. Merbach, E. Tóth, ed., The Chemistry of Contrast Agents in Medical Magnetic Resonance Imaging, John Wiley & Sons Ltd, Chichester, 2001) or as bioluminescent markers. They are also being intensively studied in nuclear medicine for the vectoring of radionuclides: copper 64, gallium 68, indium 111, technetium 99m, etc.

However, the potential value of such ligands for clinical application such as alpha radio-immunotherapy is highly limited.

Indeed, their kinetics of complexation as radioisotopes are too slow to consider obtaining radio-metal chelates capable of being speedily conveyed to physiological sites of interest. In addition, these chelates show problems of in vivo stability. Finally, the macrocycles of these ligands do not have any free nitrogen atoms for the grafting thereon of functions of coupling with biological vectors such as monoclonal antibodies which convey the radioisotopes towards the cells of interest for therapy.

To try and overcome the second problem indicated here above, numerous research studies seek to use the possibility of generating $^{212}$Bi after β disintegration of its isotopic parent namely $^{212}$Pb which has a half-life of about 11 hours, hence far longer than that of $^{212}$Bi.

However, this approach known as the "in situ $^{212}$Pb/$^{212}$Bi generator" approach requires the use of ligands capable of complexating both lead and bismuth. Now, in practice, while there are numerous lead (II) chelating structures, those capable of stably trapping bismuth (III) are far rarer. As a consequence, the number of ligands offering high affinity with these two metals is even smaller.

The affinity of polyazamacrocyclic ligands, namely the tetraazacycloalkanes ligands of the 1,4,8,11-tetraazacyclotetradecane or 1,4,7,10-tetrazacyclododecane type, as well as their unsaturated analogs, especially carboxylate baskethandle porphyrins, with lead and bismuth, have thus been studied (Z. Halime, M. Lachkar, B. Boitrel, *Biochimie*, 2009, 91, 1318-1320).

These studies have shown that only one of these porphyrin derivatives, a derivative with two basket handles functionalized by a carboxylate pendant arm, offers promising affinity with lead and bismuth. However, these studies have also shown that a bimetallic complex is obtained in the presence of lead.

In addition, the methods used to synthesize these ligands are lengthy and difficult to apply. In particular, their yields are low and they make it necessary to use chromatography purification columns and large quantities of solvents.

Above all, the solubility in an aqueous medium of chelates obtained by complexation of such porphyrin derivatives with lead, is almost zero. They therefore do not provide any answer to the third problem mentioned here above.

These prior-art ligands therefore cannot be envisaged as a means to obtain chelates liable to respond to the indispensable conditions required for clinical applications such as alpha radio-immunotherapy.

GOALS OF THE INVENTION

It is a goal of the present invention to propose specific chelates obtained by the complexation of ligands displaying high affinity with both bismuth (III) and lead (II).

In particular, it is a goal of the present invention to describe such chelates which, in at least certain embodiments, have high stability.

It is yet another goal of the present invention to describe such chelates that are soluble in aqueous medium.

It is yet another goal of the present invention to propose such chelates which, at least in certain embodiments, can find application in the context of in situ $^{212}$Pb/$^{212}$Bi or $^{213}$Bi generators.

It is yet another goal of the present invention to disclose such chelates which, in at least certain embodiments, are liable to find application, especially for trapping lead (II) or in alpha radio-immunotherapy.

SUMMARY OF THE INVENTION

These different goals or at least some of them are achieved by means of the present invention which relates to a chelate resulting from the complexation of a trans-di-N-picolinate tetraazacycloalkane ligand with a metal cation,
said ligand corresponding to the formula A:

wherein:
n is equal to 0 or to 1;
R is H or a C1-C18 alkyl radical;
R' is H or a C1-C18 alkyl radical;
and said metal cation being a cation of a metal chosen from the group constituted by lead (II) and bismuth (III).
Preferably, when R or R' is an alkyl radical, it is a C1-C6 alkyl radical.

Thus, the invention proposes chelates based on 1,4,8,11-tetraazacyclotetradecane or 1,4,7,10-tetrazacyclododecane with picolinate pendant arms. These aromatic groups, the chemical structure of which is shown here below, have the advantage of being bidentate since they possess both one nitrogen atom and one oxygen atom capable of taking part in the coordination of a metal.

It will be noted that ligands based on 1,4,8,11-tetraazacyclotetradecane or 1,4,7,10-tetrazacyclododecane and with picolinate arms have been used especially for the complexation of copper (II) and gadolinium (III) for imaging applications ((a) C. Gateau, M. Mazzanti, J. Pecaut, F. A. Dunand, L. Helm, *Dalton Trans.*, 2003, 2428-2433; (b) P. H. Fries, C. Gateau, M. Mazzanti, *J. Am. Chem. Soc.*, 2005, 127, 15801-15814; (c) L. M. P. Lima, D. Esteban-Gómez, R. Delgado, C. Platas-Iglesias, R. Tripier, *Inorg. Chem.*, 2012, 51, 6916-6927). However, the complexation of such ligands with bismuth or lead especially for therapeutic applications had not been proposed until now.

The picolinate groupings have the advantage of enabling the trapping of metal cations of lead (II) or bismuth (III) stably and of doing so even at acid pH.

In addition, owing to the bidentate character of the picolinate grouping, tetraazamacrocycle can be di-substituted only by such groupings in order to obtain the stable complexation of these metals.

Finally, such a substitution at only two of the four nitrogen atoms of these macrocycles also makes it possible to keep available the other two nitrogen atoms of the cycle for other purposes, especially with a view to coupling chelates with other molecules of interest.

Preferably, the chelate according to the invention corresponds to the formula A above in which n is equal to 0 and R is a methyl radical. The ligand then meets the following formula B.

Here below, this ligand of formula B is called DODPA when R and R' are each H and it is called Me-DODPA when R and R' are each a methyl radical.

According to one variant, said metal is a radioactive isotope chosen from the group constituted by $^{212}$Pb, $^{212}$Bi and $^{213}$Bi.

The present invention also covers any compound characterized in that it is constituted by a chelate described here above, and the metal of which is $^{212}$Pb, $^{212}$Bi or $^{213}$Bi, where at least one coupling function for coupling with an agent, especially a biological agent, has been added to at least one of the two tertiary amine functions of said ligand and/or to a carbon atom of the macrocycle.

As indicated here above, the bidentate character of the picolinate arms makes it possible to attain efficient complexation of the ligand with lead or bismuth while at the same time leaving two nitrogen atoms of the macrocycle free. These nitrogen atoms are advantageously used for the grafting of at least one coupling function, especially with a biological vector.

Preferably, this coupling function is chosen from among the following: amine, isothiocyanate, active ester (N-hydroxysuccinimide, N-hydroxyglutarimide, maleimide), carboxyl acid, activated carboxyl acid (acid anhydride, acid halogenide), alcohol, alkyne, halogenide, azide etc.

The present invention also covers any radiopharmaceutical agent comprising a chelate as described here above, the metal of which is $^{212}$Pb, $^{212}$Bi or $^{213}$Bi, to which a biological vector is coupled, by means of said coupling function, the biological vector targeting cells of interest.

Preferably, said biological vector is a monoclonal antibody.

Preferably, inter alia, said biological vector is a monoclonal antibody targeting cancer cells.

The present invention also pertains to the use of such a radiopharmaceutical agent as an alpha radio-immunotherapy agent.

Finally, the present invention is also aimed at the use of ligands as described here above for the trapping of lead (II).

DETAILED DESCRIPTION OF EMBODIMENTS OF THE INVENTION

The invention as well as the different advantages that it presents will be understood more clearly from the following description of embodiments according to this invention, given on an illustrative and non-exhaustive basis.

These embodiments are described with reference to the appended figures, of which.

SYNTHESIS OF DODPA AND ME-DODPA LIGANDS

The DODPA and Me-DODPA ligands can be synthesized according to the methods described in A. Rodríguez-Rodríguez, D. Esteban-Gómez, A. De Blas, T. Rodríguez-Blas, M. Fekete, M. Botta, R. Tripier, Platas-Iglesias, *Inorg. Chem.*, 2012, 51, 2509-2521.

A novel method of synthesis of the ligand DODPA is however proposed here. According to this method, summarized here below in the diagram 1, the cyclen 1 (1,4,7,10-tetrazacyclododecane) is made to react with glyoxal in order to obtain cyclen-dioxol 2, as a compound where only two amines in trans position can be substituted. The intermediary 2 then undergoes trans-alkylation with the ester 3 which leads to bisammonium 4 with a yield of 93%. This compound is reduced by hydrazine monohydrate which leads to the formation of a bis-acetohydrazide intermediate compound which is immediately hydrolyzed in acid medium to give the ligand DODPA with a yield of 61% calculated relative to the cyclen 1.

Diagram 1

H₂DODPA

Complexation of DODPA and Me-DODPA Ligands with Bismuth and Lead

Figure 1:
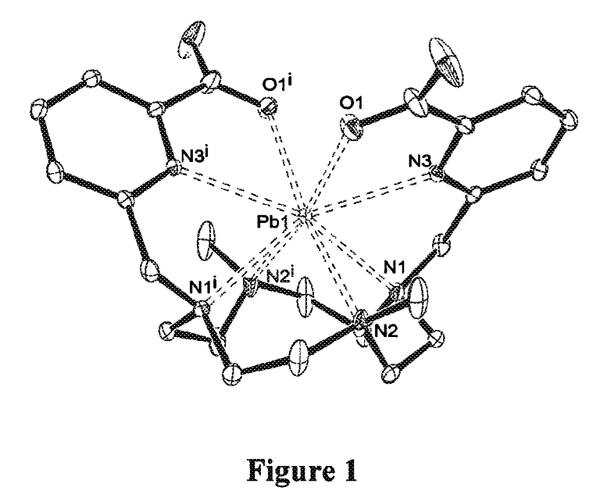
FIGS. 1 and 2 respectively represent the X-ray crystal structures of two chelates according to the invention resulting from the complexation of a ligand of formula B here above with lead (II) on the one hand (FIG. 1) and bismuth (III) on the other hand (FIG. 2). In these figures, for reasons of simplicity, the hydrogen atoms are not shown.
Figure 2:
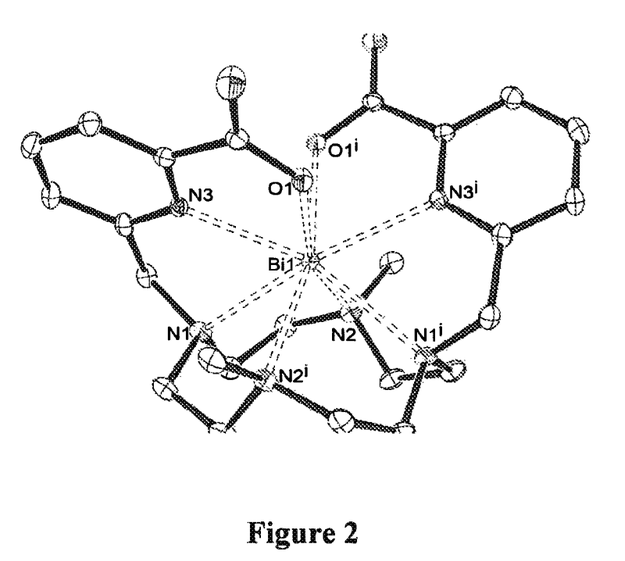

The complexation of the DODPA and Me-DODPA ligands with lead and bismuth was carried out according to the method summarized here below in the diagram 2.

and 2 respectively, were obtained by slow evaporation of aqueous solutions of the complexes isolated.

The crystals of the complexes Pb(II) present entities [Pb(Me-DODPA] and disordered water molecules while the Diagram 2

According to this method, the cyclen dipicolinate hydrochlorides DODPA.xHCl or Me-DODPA.xHCl are dissolved in water and an equivalent of $Bi(NO_3)_3.5H_2O$ is added. Then, the pH is gradually increased up to 3-4 in order to prevent the formation of insoluble bismuth hydroxides. After evaporation of water, the reaction crude product is put into methanol. The different inorganic salts precipitate and are removed by filtering. This operation is reproduced several times in order to isolate the bismuth chelate with high yield of the order of 60% to 80%.

In the same way, lead (II) complexes were obtained by adding an acid aqueous solution of $PbCl_2$ to the hydrochlorides. After a few minutes, the pH was adjusted to 6-7. After precipitation with methanol, the lead complexes (II) were isolated quasi-quantitatively.

Characteristics and Properties of Chelates Obtained

Crystalline Structures

The crystals [Pb(Me)DODPA] and [Bi(Me-DODPA)] $(NO_3).H_2O$, whose X-ray structures are shown in FIGS. 1 crystals of the complexes of Bi(III) present cations [Bi(Me-DODPA)]⁺, nitrate ions and disordered water molecules.

In these structures, the metal ions are directly linked to the eight donor atoms of the ligand. They have a syn conformation with two independent picolinate arms disposed on the same side of the macrocycle.

Table 1 here below gives certain lengths of bonds, in angstroms, between the coordination metal and the atoms referenced in FIGS. 1 and 2 for the Pb(Me-DODPA)] and [Bi(Me-DODPA)]⁺ complexes. The values between brackets correspond to the uncertainty regarding the final digit or numeric character.

TABLE 1

|  | Pb | Bi |
| --- | --- | --- |
| M(1)-O(1) | 2.692(3) | 2.390(3) |
| M(1)-N(1) | 2.727(3) | 2.633(4) |

TABLE 1-continued

|  | Pb | Bi |
|---|---|---|
| M(1)-N(2) | 2.701(4) | 2.620(4) |
| M(1)-N(3) | 2.678(3) | 2.503(4) |

Stability

For the DODPA or Me-DODPA chelates with lead (II), the thermodynamic stability constant pK was determined directly by potentiometery at 25° C., for a concentration of 0.10 M in $KNO_3$. A pK constant of 18.74 was observed for the chelate [Pb(Me-DODPA)] and 17.09 for the chelate Pb(DODPA). These values of pK were however not comparable with those of the prior-art chelate Pb(DOTA) inasmuch as this compound has a different basicity. The pM values corresponding to the non-chelated lead concentrations were therefore computed for the DODPA or Me-DODPA chelates with lead (II) and compared with the value known for the DOTA chelate with lead (II). This value pM is defined by the negative logarithm of the free metal concentration at a pH of 7.4 and with a concentration of Pb(II) of 10 µM and a ligand concentration that is ten times greater. A pM value of 12.3 was measured for the chelate of DODPA and lead (II) and 14.9 for the chelate of Me-DODPA and lead (II) while the known pM value for the complex of DOTA and lead (II) is 18.4

As regards the chelate of Me-DODPA and bismuth (III) or DODPA and bismuth (III), the thermodynamic stability constants were evaluated by NMR $^1$H (in a concentration of $10^{-2}$ M) in studying the competitivity of the complexation of bismuth (III) with Me-DODPA or DODPA and DOTA. Indeed, such a constant cannot be measured directly by potentiometery for the bismuth chelates A mole equivalent of $Bi(NO)_3$ was added to an equimolar solution of DODPA and DOTA at pH=1. The pH was then adjusted to 3 and an NMR spectrum was recorded. After five days at 25° C., it was observed that about 40% of the DODPA had been complexated with bismuth (III). This showed that the thermodynamic stability constant pK of the complex [Bi(DODPA)]$^+$ was slightly lower than that of the complex [Bi(DOTA)]$^-$ which, according to E. Csajbok, Z. Baranyai, I. Banyai, E. Brucher, R. Kiraly, A. Muller-Fahrnow, J. Platzek, B. Raduchel, M. Schafer, *Inorg. Chem.*, 2003, 42, 2342-2349, is about 30.3. On the contrary, a stability greater than that of [Bi(DOTA)]$^-$ was observed with the complex [Bi(Me-DODPA)]$^+$. Indeed, in the presence of an equimolar mixture of Me-DODPA and DOTA, the totality of the bismuth (III) was complexated by the Me-DODPA, leaving the DOTA in free ligand form.

In a second experiment, the ligand Me-DODPA in its free form was put into competition with pre-formed complex [Bi(DOTA)]$^-$, in order to remove the constraints of kinetic factor in the chelation of the metal. Trans-chelation was observed by $^1$H NMR in deuterated medium at pH 6 and at an ambient temperature for a concentration of $10^{-2}$ M. The disappearance of the NMR signals from the [Bi(DOTA)]$^-$ to the benefit of those from [Bi(Me-DODPA)]$^+$ after five days of experiment showed again that the constant of stability of the bismuth complex with Me-DODPA was greater than that of the DOTA.

These results prove that the dipicolinate ligands have a very high affinity with bismuth (III) and that they lead to highly stable complexes (stability greater than that of DOTA very particularly in the case of Me-DODPA).

Kinetics of Formation and Dissociation of Complexes

The kinetics of complexation of Me-DODPA chelates with bismuth (III) and lead (II) were studied by UV/Vis spectroscopy.

Figure 3:
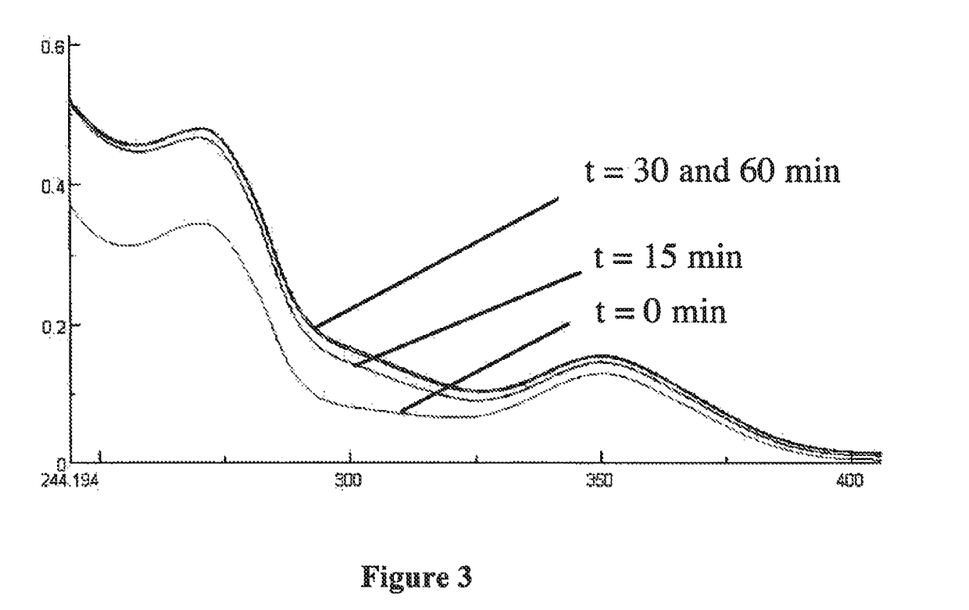
FIGS. 3 and 4 represent the UV/Vis spectra of formation and dissociation of this same ligand with bismuth (FIG. 3) and lead (FIG. 4)
Figure 4:
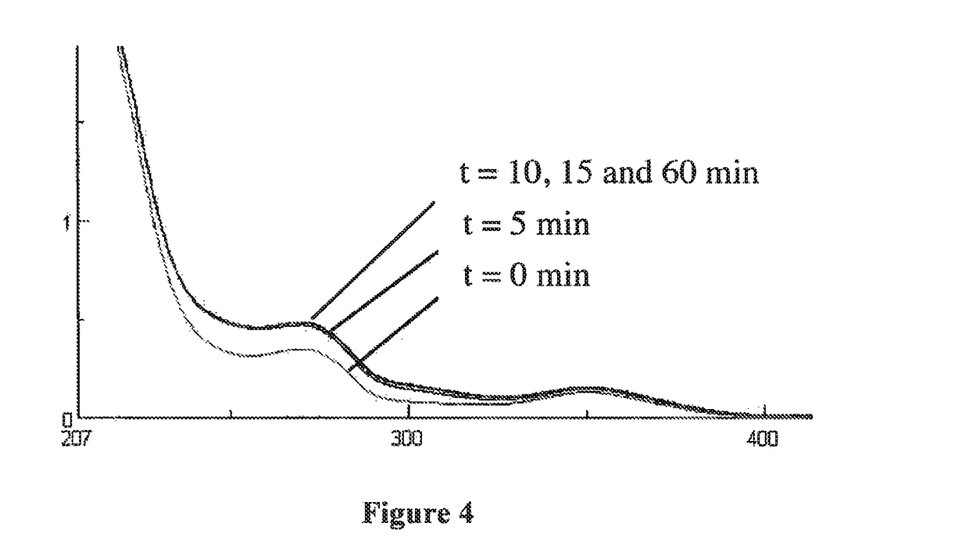

The UV spectra are represented in FIGS. 3 and 4 respectively.

An aqueous solution of $Bi(NO_3)_3.5H_2O$ ($1.65 \times 10^{-4}$ M) was added to an aqueous solution of Me-DODPA ($1.65 \times 10^{-4}$ M). The UV/Vis spectra were recorded at different reaction times. As can be seen in FIG. 3, the total complexation of Me-DODPA with bismuth (III) was observed after 30 minutes of stirring at ambient temperature.

Referring to FIG. 4, a total complexation of Me-DODPA with lead (II) was observed ten minutes after the equimolar mixing ($0.74 \times 10^{-4}$ M) of an aqueous solution of $PbCl_2$ and an aqueous solution of Me-DODPA at pH=7.

The results show that the picolinate arm ligands very rapidly complexate the heavy metals, whether it is bismuth (III) or lead (II). In the case of bismuth (III), the kinetics of complexation are far higher than that observed with the prior-art ligands such as DOTA.

The kinetics of dissociation of these complexes were also studied by NMR. In this context, the [Bi(Me-DODPA)] ($NO_3$) and [Pb(Me-DODPA)] complexes were dissolved in DCl 0.1 M.

For the [Bi(Me-DODPA)]($NO_3$), no dissociation whatsoever was observed even after a few days whereas a total dissociation of the complex [Pb(Me-DODPA)] was observed at the end of seven days.

These results show that it is possible according to the invention to obtain stable chelates for both lead (II) and bismuth (III) from one and the same ligand.

Moreover, such chelates, which are water-soluble, can be used to make radiopharmaceutical agents, especially radiopharmaceutical agents that can be used in alpha radioimmunotherapy inasmuch as they have nitrogen atoms available for the grafting of biological vectors. Such grafting is thus made very simple by classic techniques accessible to those skilled in the art by the replacing, for example, of one of the methyl (R or R') arms by an ethylamine or propylamine arm. The best results obtained with Me-DODPA compared with its DODPA analog show that the presence of tertiary amines exalts the physical-chemical properties of the chelate, making such future vectoring favorable.

Preparation of the Radio-labeled Chelate ($^{213}$Bi(Me-DODPA))$^+$ and Study of its In Vitro Stability.

The labeling of this chelate was evaluated by thin-layer chromatography (TLC) (eluent: MeOH/NH$_4$Cl (20%); 1/1) and by reverse-phase high-performance liquid chromatography (HPLC) using a Kromasil $C_{18}$ column (linear gradient of TFA (0.01% of water)-CH$_3$CN for 20 minutes) and activity was detected with an NaI gamma scintillator.

A solution of Me-DODPA$^{2-}$ (0.115 at 3.5 nmol) buffered at pH 7.4 was added to an eluate of $^{213}$Bi (100 to 500 µL), the activity of which ranges from 3 to 12 MBq. A computed volume of ascorbate solution at pH 7.4 was added to obtain samples of concentration at 50 mM. The mixtures were incubated for 15 minutes at ambient temperature and at 90° C.

Figure 5:
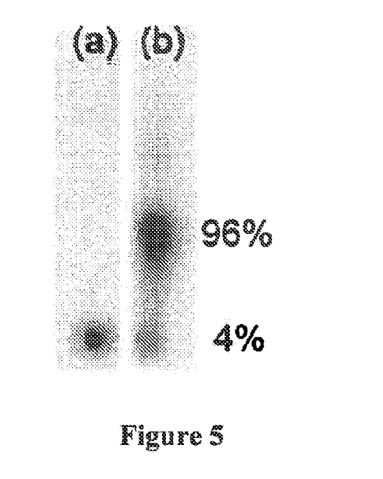
FIG. 5 represents a thin-layer chromatograph of $^{213}$Bi and of the chelate $^{213}$Bi-Me-DODPA.

Referring to FIG. 5, TLC analysis shows that free $^{213}$Bi has a frontal ratio (Fr) of 0 (a) and that the chelate ($^{213}$Bi (Me-DODPA))$^+$ has an Fr value of 0.5 (b).

Figure 6:
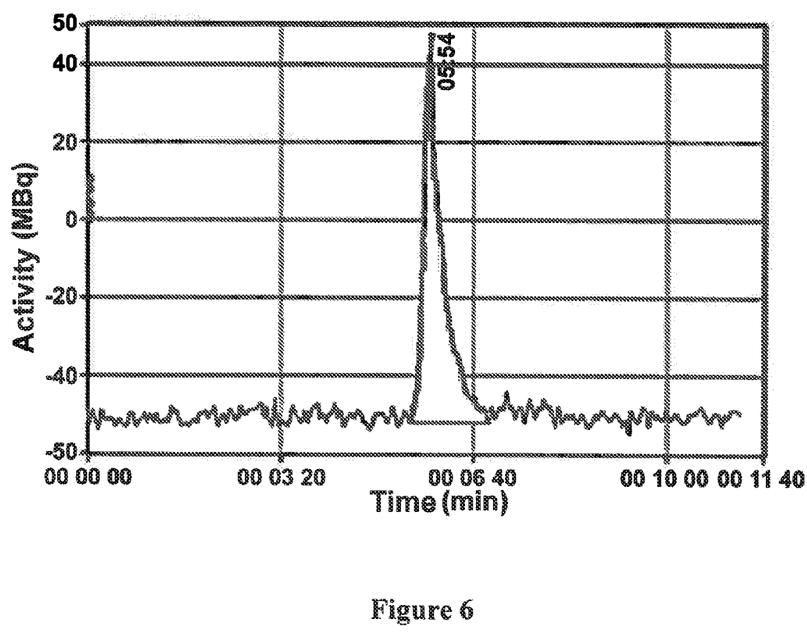
FIG. 6 represents the HPLC chromatogram of this same chelate.

Referring to FIG. 6, an HPLC analysis with a retention time for the ($^{213}$Bi(Me-DODPA))$^+$ chelate of about 5.5 minutes shows that the free $^{213}$Bi has no affinity for the C$_{18}$ column.

The results of these experiments show a better chelation yield when the chelation is done at 90° C. (radioactivity associated with the ligand at 91% to 96%) than when it is done at ambient temperature (radioactivity associated with the ligand at 60%) in using an activity/ligand ratio of 30 to 40 MBq/nmol for the preparation of this chelate.

The stability of the serum and of the in vitro chelate were also studied by TLC and by HPLC.

For the stability of the serum, 200 μL of radiomarked Me-DODPA$^{2-}$ solution (activity: 1 MBq, radiochemical purity: 95%) were mixed with 800 μL of human plasma. The plasma stability values were controlled in comparison with free $^{213}$Bi, after 1 and 2 hours of incubation (about 1 and 2 half-lives) at ambient temperature by direct gel permeation chromatography on plasma in a PD-10 column and by TLC analysis of this supernatant after precipitation of the plasma proteins with ammonium sulfate. The TLC analysis was performed under the same conditions as earlier. After precipitation, the activity in the precipitate was measured (78.8%) as also the activity in the supernatant (3.8%).

Figure 7:
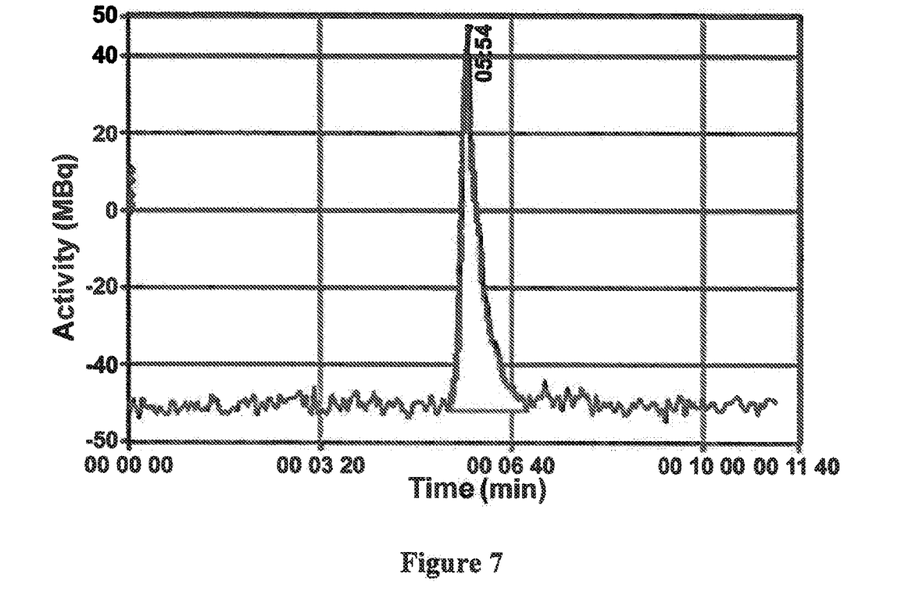
FIG. 7 represents the gel permeation chromatogram of the same chelate in the presence of human plasma.

Referring to FIG. 7 which shows the gel permeation chromatogram of the plasma containing free $^{213}$Bi and the complex ($^{213}$Bi(Me-DODPA))$^+$, the chromatograms show the presence of molecules of low molecular weight (<10 kDa).

Figure 8:
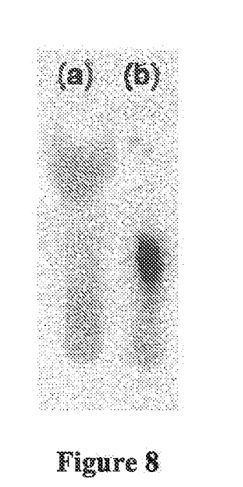
FIG. 8 represents a thin layer chromatograph of the chelate $^{213}$Bi-Me-DODPA in the supernatant after precipitation of proteins.

Referring to FIG. 8, the TLC analysis of the supernatant shows that there was no free $^{213}$Bi (Rf=0) and that the chelate of ($^{213}$Bi(Me-DODPA))$^+$ is present in this supernatant. Indeed, more than 90% of the radioactivity is detected at the level Fr=0.5.

The results show that the chelate ($^{213}$Bi(Me-DODPA))$^+$ is largely present and is stable in human plasma for at least two half-lives.

These results show that it is possible according to the invention to carry out chelation of $^{213}$Bi with the ligand Me-DODPA$^{2-}$ qualitatively and quantitatively.

In addition, such chelates are stable in human plasma and can therefore be used to make radiopharmaceutical agents, especially radiopharmaceutical agents that can be used in alpha radio-immunotherapy.

The invention claimed is:

1. Chelate resulting from the complexation of a trans-di-N-picolinate tetraazacycloalkane ligand with a metal cation, said ligand corresponding to the formula A:

wherein:
n is equal to 0 or to 1;
R is H or a C1-C18 alkyl radical;
R' is H or a C1-C18 alkyl radical;
said metal cation being a cation of a metal chosen from the group constituted by lead (II) and bismuth (III).

2. Chelate according to claim 1, characterized in that said chelate corresponds to the formula A in which n is equal to 0 and R is a methyl radical.

3. Chelate according to claim 1, characterized in that said metal is a radioactive isotope chosen from the group constituted by $^{212}$Pb, $^{212}$Bi and $^{213}$Bi.

4. The chelate of claim 1, further comprising: at least one coupling function coordinated to at least one of the two amine functions of said ligand bearing the R radical and the R' radical, by substitution of the R radical or the R' radical, wherein the coupling function is bonded to an agent.

5. The chelate of claim 4, wherein the coupling function is chosen from among the following functions: amine; isothiocyanate; active ester; carboxyl acid; activated carboxyl acid; alcohol; alkyne; halogenide; or azide.

6. The chelate of claim 4, wherein the agent is a biological vector targeting cells of interest of the human or animal body.

7. The chelate of claim 6, wherein the biological vector is a monoclonal antibody.

8. The chelate of claim 7, wherein the cells of interest of the human or animal body are cancer cells.

9. Method of delivering alpha radio-immunotherapy to a subject, comprising:
providing a subject;
complexing a trans-di-N-picolinate tetraazacycloalkane ligand with a $^{212}$Pb(II) cation, said ligand corresponding to the formula A:

wherein:
n is equal to 0 or to 1;
R is H or a C1-C18 alkyl radical;
R' is H or a C1-C18 alkyl radical;
coordinating of at least one of the two amine functions of said ligand bearing the R radical and the R' radical, by substitution of the R radical or the R' radical, to one coupling function, said coupling function being bonded to a biological vector targeting cells of the subject; and,
β-desintegration of said $^{212}$Pb(II) cation into a $^{212}$Bi (III) cation.

10. Method of trapping lead II comprising a step of complexation of a trans-di-N-picolinate tetraazacycloalkane ligand with a Pb(II) cation, said ligand corresponding to the formula A:

wherein:

n is equal to 0 or to 1;

R is H or a C1-C18 alkyl radical; and

R' is H or a C1-C18 alkyl radical.

11. The chelate of claim 5, wherein the active ester is selected from: N-hydroxysuccinimide, N-hydroxyglutarimide, or maleimide.

12. The chelate of claim 5, wherein the activated carboxyl acid is selected from: acid anhydride or acid halogenide.

* * * * *